(12) United States Patent
Meyer et al.

(10) Patent No.: US 8,361,140 B2
(45) Date of Patent: Jan. 29, 2013

(54) HIGH STRENGTH LOW OPENING PRESSURE STENT DESIGN

(75) Inventors: Michael P. Meyer, Richfield, MN (US); Alison Julson, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 69 days.

(21) Appl. No.: 12/980,750

(22) Filed: Dec. 29, 2010

(65) Prior Publication Data

US 2011/0160843 A1 Jun. 30, 2011

Related U.S. Application Data

(60) Provisional application No. 61/290,800, filed on Dec. 29, 2009.

(51) Int. Cl.
*A61F 2/82* (2006.01)
(52) U.S. Cl. .............. 623/1.15; 623/1.16; 623/1.17; 623/1.3
(58) Field of Classification Search .......... 623/1.15, 623/1.16, 1.2, 1.3; *A61F 2/82*
See application file for complete search history.

(56) References Cited

U.S. PATENT DOCUMENTS

| | | |
|---|---|---|
| 5,091,205 A | 2/1992 | Fan |
| 5,383,892 A | 1/1995 | Cardon et al. |
| 5,601,593 A | 2/1997 | Freitag |
| 5,807,404 A | 9/1998 | Richter |
| 5,843,120 A | 12/1998 | Israel et al. |
| 5,843,172 A | 12/1998 | Yan |
| 5,855,600 A | 1/1999 | Alt |
| 5,972,027 A | 10/1999 | Johnson |
| 6,036,725 A | 3/2000 | Avellanet |
| 6,042,606 A | 3/2000 | Frantzen |
| 6,096,070 A | 8/2000 | Ragheb et al. |
| 6,120,534 A | 9/2000 | Ruiz |
| 6,168,621 B1 | 1/2001 | Vrba |
| 6,206,911 B1 | 3/2001 | Milo |
| 6,264,687 B1 | 7/2001 | Tomonto |
| 6,315,708 B1 | 11/2001 | Salmon et al. |
| 6,336,937 B1 | 1/2002 | Vonesh et al. |
| 6,409,750 B1 | 6/2002 | Hyodoh et al. |
| 6,451,052 B1 | 9/2002 | Burmeister et al. |
| 6,485,507 B1 | 11/2002 | Walak et al. |
| 6,488,702 B1 | 12/2002 | Besselink |
| 6,545,097 B2 | 4/2003 | Pinchuk et al. |
| 6,579,306 B1 | 6/2003 | Voelker et al. |
| 6,582,461 B1 | 6/2003 | Burmeister et al. |
| 6,767,360 B1 | 7/2004 | Alt et al. |
| 6,890,350 B1 | 5/2005 | Walak |

(Continued)

FOREIGN PATENT DOCUMENTS

| | | |
|---|---|---|
| EP | 1302179 A2 | 4/2003 |
| WO | 9531945 | 11/1995 |

(Continued)

*Primary Examiner* — Christopher D. Koharski
*Assistant Examiner* — Jason-Dennis Stewart
(74) *Attorney, Agent, or Firm* — Vidas, Arrett & Steinkraus

(57) ABSTRACT

A stent has a plurality of expansion columns that extend in a radial direction to form a circumference of the stent and interconnected in the axial direction to form an overall axial length of the stent. Each expansion column has a plurality of first cells and a plurality of second cells that alternates along the expansion column with at least one first cell. Each first cell has at least two facing walls extending in the radial direction that have a first width. The second cells each have at least two facing walls that extend in the radial direction which have a second with greater than the first width. The first cell uses less force to open than the second cell, but upon opening provides increased radial strength by creating a substantially vertical cell wall.

15 Claims, 10 Drawing Sheets

U.S. PATENT DOCUMENTS

| | | |
|---|---|---|
| 6,899,729 B1 | 5/2005 | Cox et al. |
| 7,435,255 B1 | 10/2008 | Rao |
| 2002/0068969 A1 | 6/2002 | Shanley et al. |
| 2003/0109887 A1 | 6/2003 | Galdonik et al. |
| 2003/0195606 A1 | 10/2003 | Davidson et al. |
| 2003/0208263 A1 | 11/2003 | Burmeister et al. |
| 2004/0034402 A1 | 2/2004 | Bales et al. |
| 2004/0073251 A1 | 4/2004 | Weber |
| 2004/0117002 A1 | 6/2004 | Girton et al. |
| 2004/0267352 A1 | 12/2004 | Davidson et al. |
| 2005/0038498 A1 | 2/2005 | Dubrow et al. |
| 2006/0293743 A1 | 12/2006 | Andersen et al. |
| 2008/0097571 A1 | 4/2008 | Denison et al. |

FOREIGN PATENT DOCUMENTS

| | | |
|---|---|---|
| WO | 9626689 | 9/1996 |
| WO | 9727898 | 8/1997 |
| WO | 9822159 | 5/1998 |
| WO | 0108600 | 2/2001 |
| WO | 0135864 | 5/2001 |
| WO | 0168158 | 9/2001 |
| WO | 0224247 | 3/2002 |
| WO | 0243788 | 6/2002 |
| WO | 03026532 | 4/2003 |
| WO | 2005046749 | 5/2005 |
| WO | 2005077430 | 8/2005 |

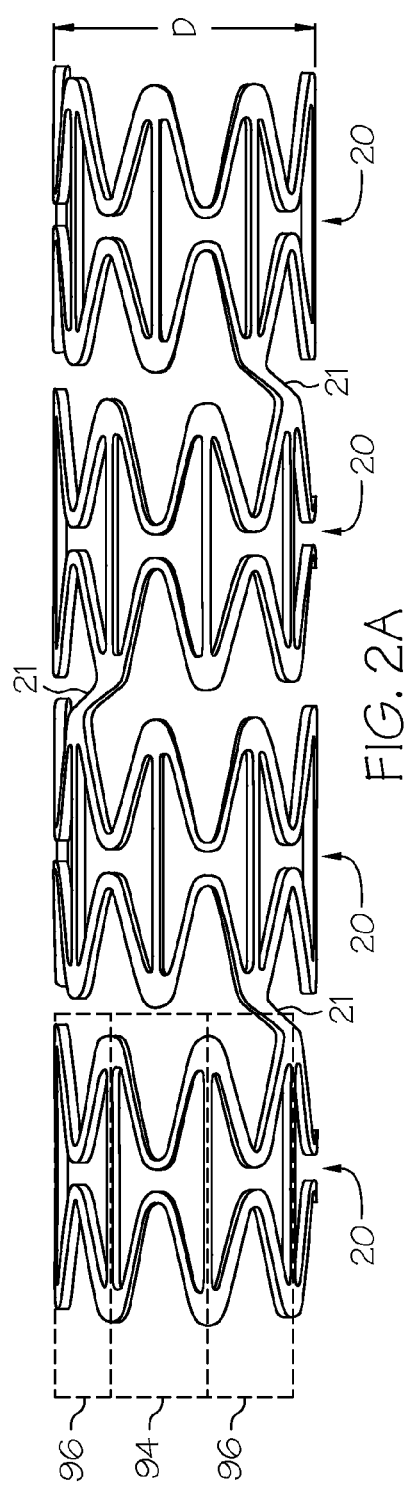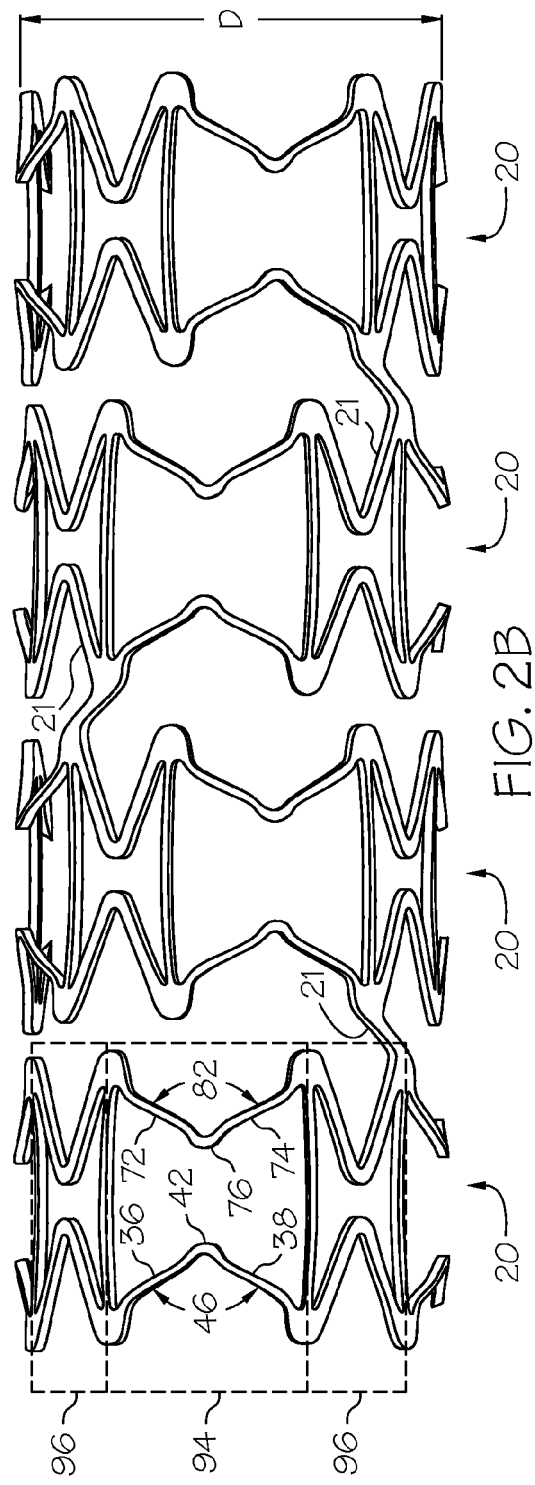

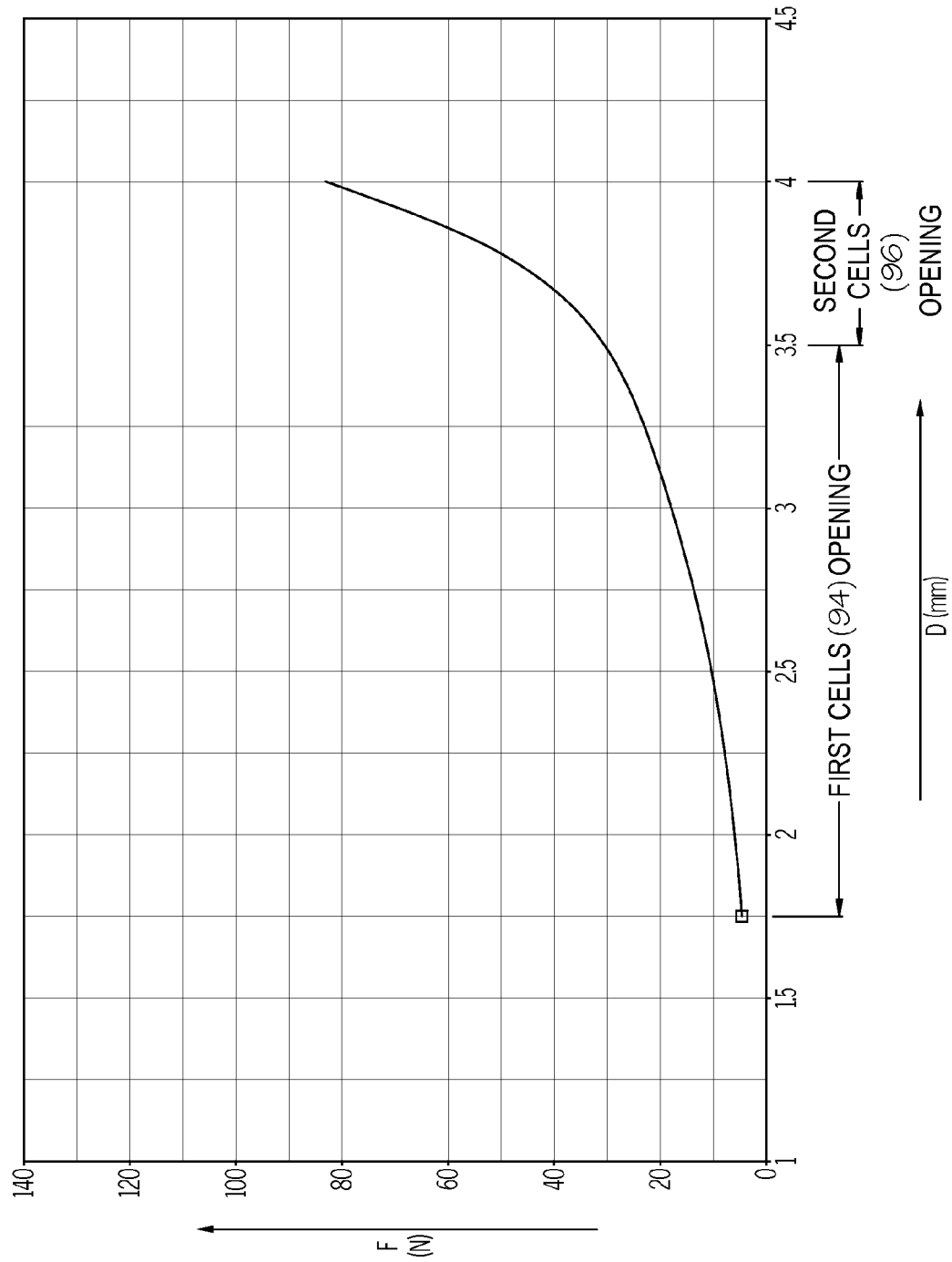

HIGH STRENGTH LOW OPENING PRESSURE STENT DESIGN

CROSS-REFERENCE TO RELATED APPLICATIONS

Not applicable

BACKGROUND

A stent is a medical device introduced into a body lumen and is well known in the art. A stent is typically delivered in an unexpanded state to a desired location in a bodily lumen and then expanded by an internal radial force.

Stents, grafts, stent-grafts, vena cava filters, expandable frameworks, and similar implantable medical devices, collectively referred to hereinafter as stents, are radially expandable endoprostheses, which are typically intravascular implants capable of being implanted transluminally and enlarged radially after being introduced percutaneously. Stents may be implanted in a variety of bodily lumens or vessels such as within the vascular system, urinary tracts, bile ducts, fallopian tubes, coronary vessels, secondary vessels, etc. Stents can be balloon-expandable, self-expanding or a combination of self-expanding and balloon-expandable (or "hybrid expandable").

Radial strength and opening forces are closely related to one another in stent design. In traditional stent designs, where a high radial strength is desired, a high opening force is needed. Typically where a low opening force is desired, the stent will have a low radial strength.

BRIEF SUMMARY

In at least one embodiment of the stent, a stent has a proximal end, a distal end, a length along a longitudinal axis extending through the proximal and distal ends, and a circumference. A plurality of expansion columns that extend in a radial direction form the circumference of the stent. The expansion columns are interconnected in the axial direction to form the length of the stent. In this embodiment, each column comprises a plurality of first cells and a plurality of second cells. Each second cell alternates along the expansion column with at least one first cell. Each first cell has at least two facing walls that extend in the radial direction, and each second cell has at least two facing walls that extend in the radial direction. The two facing walls of the second cells have a greater rigidity, or resistance to opening, than the two facing walls of the first cells. The first cell requires a lower opening force than the second cell, but upon opening provides radial strength by creating a substantially vertical cell wall. In various embodiments that will be described below, the second cell can provide additional radial strength by having an increased strut width or wall thickness at these portions of the stent, decreasing the length of certain segments of the stent, or adding restraints along the edges of the expansion columns. This configuration allows the stent to have high radial strength while using a low deployment force.

BRIEF DESCRIPTION OF THE DRAWING(S)

FIGS. 2A-2D are perspective views of the stent shown in FIG. 1 bisected along the longitudinal axis of the stent, each figure showing the stent at a different stage of expansion.

FIG. 3 is a graph of the diameter of the stent versus the expansion force needed for the expansion of the stent as shown in FIGS. 2A-2D.

DETAILED DESCRIPTION

Figure 1:
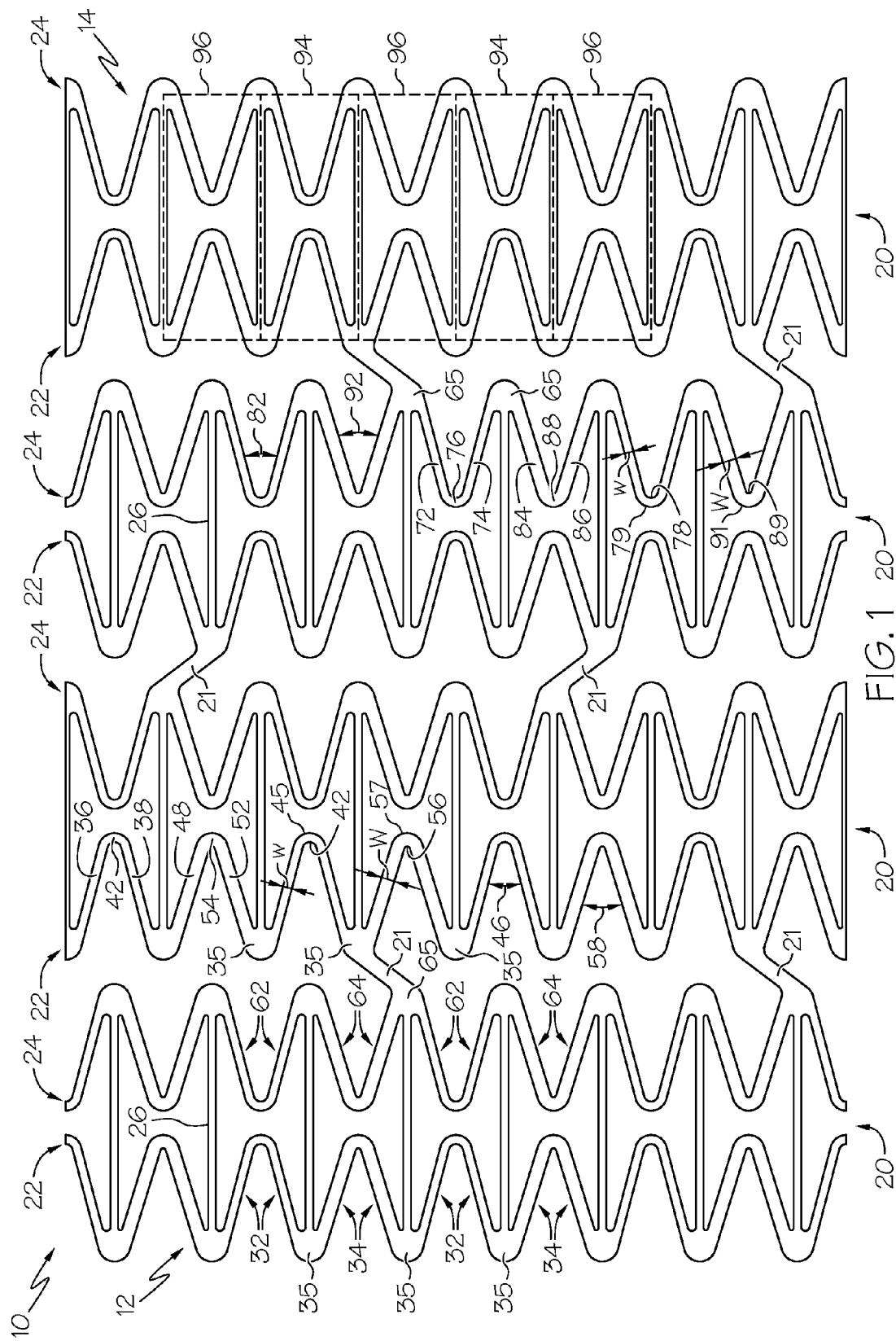
FIG. 1 is a flat view of an embodiment of the stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

One embodiment of the stent of the present invention, stent 10, is shown in FIG. 1 in an unexpanded state. Although stent 10 is shown in a flat view in FIG. 1, stent 10 is a cylindrical member having proximal end 12, a distal end 14 and a circumference (not shown). Stent 10 comprises at least a plurality of interconnected expansion columns 20, each of which extends radially to form the circumference of stent 10. Each expansion column 20 is connected to a longitudinally adjacent expansion column 20 by at least one interconnecting strut 21. While FIG. 1 only shows four expansion columns 20, in some embodiments fewer or greater numbers of expansion columns form the axial length of the stent from proximal end 12 to distal end 14.

In the embodiment shown in FIG. 1, each expansion column 20 comprises first serpentine band 22, second serpentine band 24, and at least one connecting strut 26. As shown in FIG. 1, first serpentine band 22 has a first strut pair 32 connected to at least an adjacent second strut pair 34 at connecting member 35. In some embodiments, such as the one shown in FIG. 1, connecting strut 26 is also joined with first serpentine band 22 at connecting member 35. Also, in some embodiments, including FIG. 1, connecting member 35 serves to join interconnecting strut 21 with a first expansion column 20.

First strut pair 32 of first serpentine band 22 has at least a first strut 36 and a second strut 38 joined together by a linking member 42. In the embodiment shown in FIG. 1, first strut 36, second strut 38 and linking member 42 of first strut pair 32 each have a first strut width, w. Strut width w is a narrow strut width. Although FIG. 1 shows that the first strut widths w of first strut 36, second strut 38 and linking member 42 are equivalent, in other embodiments the strut widths of members 36, 38, 42 vary relative to one another as long as their respective strut widths remain narrower than the strut width of second strut pair 34 as will be discussed below.

In the embodiment shown in FIG. 1, first strut 36 and second strut 38 are also generally straight members, while linking member 42 is a curved member having inner radius 44 and outer radius 45. In other embodiments of the invention, other strut pair configurations can be utilized. In some embodiments, when connected together by linking member 42, first strut 36 and second strut 38 form opening angle 46. In the embodiment shown in FIG. 1, opening angle 46 opens in the direction of proximal end 12. In at least one embodiment, opening angle 46 is an acute angle in the unexpanded state.

Second strut pair 34 is connected to first strut pair 32 at connecting member 35, as shown in FIG. 1. Second strut pair 34 has at least a first strut 48 and a second strut 52 that are coupled together with linking member 54. As shown in FIG. 1, first strut 48, second strut 52 and linking member 54 of second strut pair 34 each have a second strut width, W. In at least one embodiment, second strut width W is greater than first strut width w (or, conversely, first strut width w is less than second strut width W). Although FIG. 1 shows that the second strut widths of first strut 48, second strut 52 and linking member 54 are equivalent, in other embodiments the strut widths of members 48, 52, 54 can vary relative to one another as long as their respective strut widths are wider as compared with first strut pair 32.

In FIG. 1, first strut 48 and second strut 52 are generally straight members, while linking member 54 is a curved member having inner radius 56 and outer radius 57. In other embodiments of this invention, other strut pair configurations can be utilized. In some embodiments, when connected together by linking member 54, first strut 48 and second strut 52 form opening angle 58. In the embodiment shown in FIG. 1, opening angle 58 opens in the direction of proximal end 12, just like opening angle 46 of first strut pair 32. In at least one embodiment, opening angle 58 is an acute angle in the unexpanded state. As shown in FIG. 1, opening angle 58 and opening angle 46 are approximately equivalent. In at least one embodiment, the lengths of first strut 36 and second strut 38 of first strut pair 32 are approximately equivalent. Further, in at least one embodiment, the lengths of first strut 48 and second strut 52 of second strut pair 34 are approximately equivalent. In at least the embodiment shown in FIG. 1, the lengths of first strut 48 and second strut 52 of second strut pair 34 are approximately equivalent to the lengths of first strut 48 and second strut 52 of second strut pair 34. In the embodiment shown in FIG. 1, first strut pair 32 is similar to second strut pair 34, except that first strut pair 32 is narrower than second strut pair 34.

Turning now to the second serpentine band 24, second serpentine band 24 also has first strut pair 62 connected to at least an adjacent second strut pair 64 at connecting member 65, as shown in FIG. 1. As previously discussed, in some embodiments, second serpentine band 24 is connected to first serpentine band 22 with at least one connecting strut 26. In some embodiments, such as the one shown in FIG. 1, connecting strut 26 is also joined with first serpentine band 24 at connecting member 65. Also, in some embodiments (including FIG. 1), connecting member 65 of first expansion column 20 joins interconnecting strut 21 with a second expansion column 20.

First strut pair 62 of second serpentine band 24 has at least a first strut 72 and at least a second strut 74 joined together with linking member 76. In the embodiment shown in FIG. 1, first strut 72, second strut 74 and linking member 76 of first strut pair 62 each have a first strut width, w. Although FIG. 1 shows that the first strut widths w of first strut 72, second strut 74 and linking member 76 are equivalent, in other embodiments the strut widths of members 72, 74, 76 can vary relative to one another as long as their respective strut widths remain narrow as compared with the strut width of second strut pair 64 as will be discussed below. In the embodiment shown, first strut width w of first strut pair 62 of second serpentine band 24 is approximately equivalent to first strut width w of first strut pair 32 of first serpentine band 22.

As shown in FIG. 1, first strut 72 and second strut 74 are generally straight members, while linking member 76 is a curved member having inner radius 78 and outer radius 79. In other embodiments, other strut pair configurations can be utilized. In some embodiments, when connected together by linking member 76, first strut 72 and second strut 74 form opening angle 82. In the embodiment shown in FIG. 1, opening angle 82 opens in the direction of distal end 14. As shown in this figure, opening angle 82 is an acute angle in the unexpanded state. In some embodiments, such as the one shown in FIG. 1, opening angle 82 is equivalent to opening angle 46 of first strut pair 32 of first serpentine band 22. In the embodiment shown in FIG. 1, first strut pair 32 of first serpentine band 22 effectively mirrors first strut pair 62 of second serpentine band 24.

Second strut pair 64 is connected to first strut pair 62 at connecting node 65, as shown in FIG. 1. Second strut pair 64 of second serpentine band 24 has at least a first strut 84 and a second strut 86 that are coupled together with linking member 88. In the embodiment shown, first strut 84, second strut 86 and linking member 88 of second strut pair 64 each have a second strut width, W. As shown in FIG. 1, second strut width W is greater than first strut width w. In at least one embodiment, second strut width W is greater than first strut width w (or, conversely, first strut width w is less than second strut width W). Although FIG. 1 shows that the second strut widths of first strut 84, second strut 86 and linking member 88 are equivalent, in other embodiments the strut widths of these members 84, 86, 88 can vary relative to one another as long as their respective strut widths are wider than struts 72, 74 of first strut pair 62.

In at least one embodiment, such as the embodiment shown in FIG. 1, second strut width W of second strut pair 64 of second serpentine band 24 is approximately equivalent to second strut width W of second strut pair 34 of first serpentine band 22. As shown in FIG. 1, first strut 84 and second strut 86 of second strut pair 64 are generally straight members, while linking member 88 is a curved member having inner radius 89 and outer radius 91. In other embodiments, other strut pair configurations can be utilized. In some embodiments, when connected together by linking member 88, first strut 84 and second strut 86 form opening angle 92. In the embodiment shown in FIG. 1, opening angle 92 opens in the direction of distal end 14. As shown in this figure, opening angle is an acute angle in the unexpanded state. In some embodiments, such as the one shown in FIG. 1, opening angle 92 is equivalent to opening angle 58 of first strut pair 34 of first serpentine band 22. In the embodiment shown in FIG. 1, second strut pair 34 of first serpentine band 22 effectively mirrors first strut pair 64 of second serpentine band 24.

As shown in FIG. 1, opening angle 82 and opening angle 92 are also approximately equivalent. In at least one embodiment, the lengths of first strut 72 and second strut 74 of first strut pair 62 are approximately equivalent. Further, in at least one embodiment, the lengths of first strut 84 and second strut 86 of second strut pair 64 are approximately equivalent. In at least the embodiment shown in FIG. 1, the lengths of first strut 72 and second strut 74 of first strut pair 62 are approximately equivalent to the lengths of first strut 84 and second strut 86 of second strut pair 64. In the embodiment shown in FIG. 1, first strut pair 62 is similar to second strut pair 64, except that first pair 62 is narrower than second strut pair 64.

In the embodiment shown, at least first strut pair 32 of first serpentine band 22 and first strut pair 62 of second serpentine band 24 form the walls of a first cell 94 of expansion column 20. In this embodiment, because first strut pairs 32, 62 have struts with a narrower strut width w than second strut pairs 34, 64, the walls of first cell 94 form a thinly-walled first cell 94. In at least one embodiment, first cell 94 can be further defined by connecting struts 26, where applicable. As shown in FIG. 1, connecting struts 26 have a similar strut width, w, to first strut pair 32 of first serpentine band 22 and first strut pair 62 of second serpentine band 24. However, in some embodiments, connecting struts 26 has a different strut width than first strut pair 42 of first serpentine band 22 and first strut pair 62 of second serpentine band 24 depending on the desired axial strength or flexibility of stent 10.

Also, in at least one embodiment such as the one shown in FIG. 1, at least second strut pair 34 of first serpentine band 22 and second strut pair 64 of second serpentine band 24 form the walls of a second cell 96 of expansion column 20. Because second strut pairs 34, 64 have struts with a wider strut width W than first strut pairs 32, 62, the walls of second cell 96 form a thicker-walled cell than first cell 94. In at least one embodiment, second cell 96 can be further defined by connecting struts 26, where applicable.

In at least one embodiment, the thicker-walled second cells 96 alternate with at least one thinly-walled first cell 94 along expansion column 20, as shown in FIG. 1. Thicker-walled second cells 96 have a greater rigidity than the thinly-walled first cells 94. Thus, the thinly-walled first cells 94 use a lower deployment force than the thicker-walled second cells 96 in order to expand. Such a design allows for a two-stage deployment mechanism: thinly-walled first cells 94 can expand (or "open") at low pressure using a low deployment force to reach a nominal stent diameter, while thicker-walled second cells 96 can later open with additional pressure if needed to increase the diameter of stent 10 for proper sizing within the body lumen. Also, this design provides additional radial strength because, as the thinly-walled first cells 94 are opened, opening angles 46, 82 increase until each strut pair 32, 62 of first cell 94 forms a substantially vertical member.

While the above disclosure describes a thinly-walled first cell 94 formed from first strut pairs 32, 62 with a strut width that is narrower than the strut width of the second strut pairs 34, 64, in at least one embodiment of the invention first cells 94 is formed with strut pairs 32, 62 having thinner wall thicknesses than second strut pairs 34, 64. In at least one embodiment, thinly-walled first cell 94 is formed from first strut pairs 32, 62 with both a strut width that is narrower than the strut width of the second strut pairs 34, 64 and a wall thickness that is thinner than the wall thickness of the second strut pairs 34, 64. In at least one embodiment, thinly-walled first cell 94 is formed from first strut pairs 32, 62 that are longer and narrower than second strut pairs 34, 64. In all of these aforementioned embodiments, second cell 96 is more rigid, or more resistant to opening, than first cell 94.

Figure 2C:
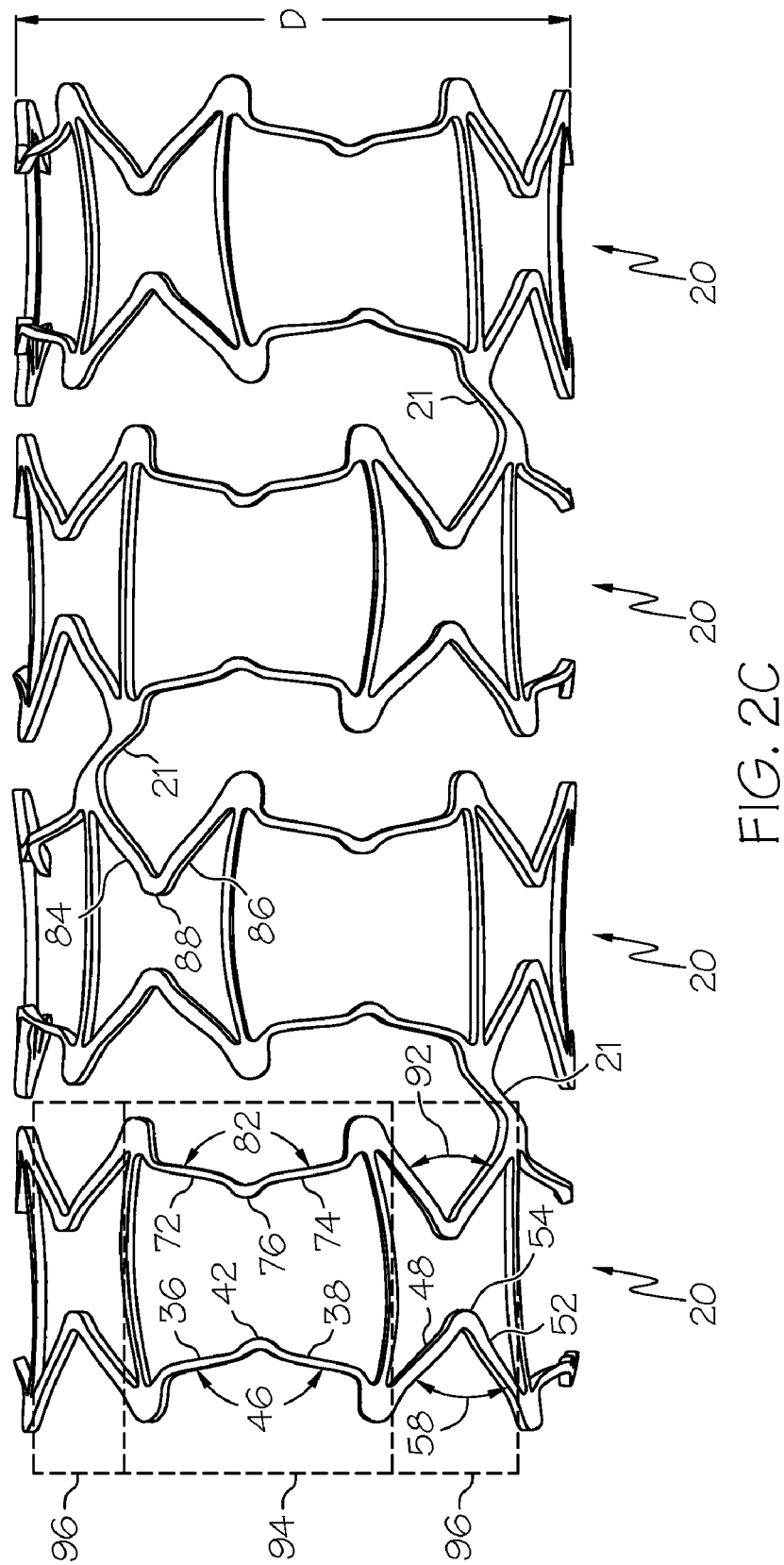

FIGS. 2A-2D illustrate the expansion stages of stent 10 of FIG. 1 during deployment of stent 10. FIG. 2A shows a perspective view of stent 10 of FIG. 1 in an unexpanded state prior to deployment. The stent 10 in FIG. 2A is shown as a section bisected along an axis of stent 10 in order to simplify the depiction of the various expansion stages of the stent. FIG. 2A shows a plurality of expansion columns 20, each expansion column having first cells 94 that alternate with second cells 96. Stent 10 has an outer diameter D in the unexpanded state prior to deployment.

Figure 2D:
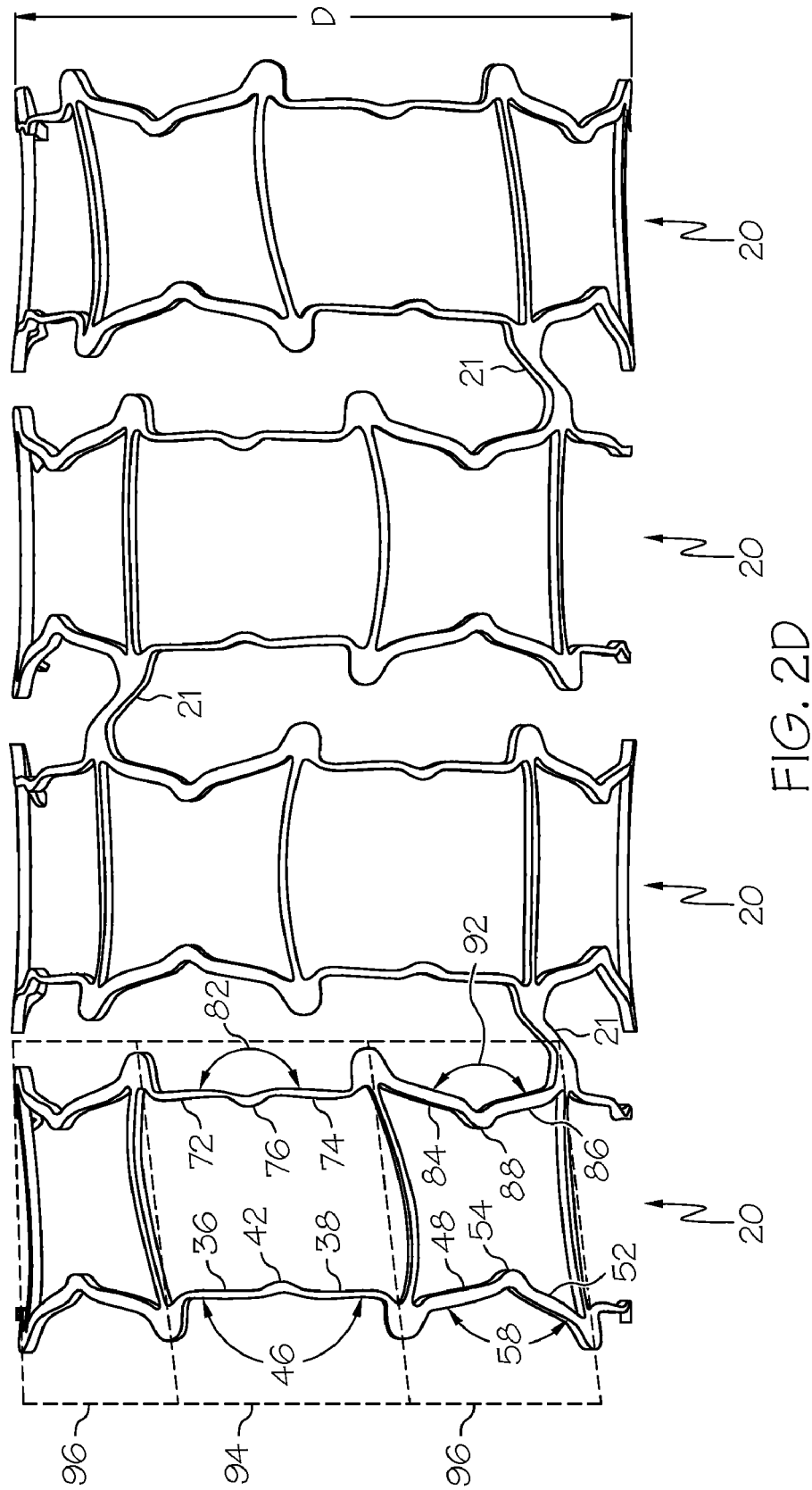

In at least one embodiment of this invention, once a radially expansive force is applied to stent 10 during deployment (such as with a balloon or via self-expansion or both), as shown in FIG. 2B, first cells 94 throughout stent 10 begin to "open," meaning first cell 94 expands such that the opening angle 46 between first strut 36 and second strut 38 (and, likewise, the opening angle 82 between first strut 72 and second strut 74) increases. However, as first cells 94 begin to expand, the radially expansive force is not enough to open thicker-walled second cells 96. As the radially expansive force is applied and first cells 94 begin to open, diameter D increases. As the radially expansive force increases, diameter D further increases and first cells 94 continue to open such that first strut 36 and second strut 38 (and, likewise, first strut 72 and second strut 74) form a substantially vertical cell wall. In other words, first cells 94 continue to open such that opening angle 46 (and, likewise, opening angle 82) is approximately between 175° and 180° (degrees). Because of the construction of strut pairs 32, 62 in some embodiments, particularly the curved shape of linking members 42, 76, opening angle 46 will never reach 180° (degrees). At this point, diameter D reaches the nominal stent diameter. If the diameter D is insufficient for the inner diameter of the lumen where stent 10 is deployed, diameter D can be increased with application of additional force. As shown in FIG. 2C, when the first cells form substantially vertical cell walls, the second cells 96 begin to open with the application of additional force. As second cells 96 open, diameter D continues to increase with this additional force. FIG. 2D shows stent 10 fully expanded at a maximum diameter D.

FIG. 3 graphically compares the force applied (shown on the y-axis) with the outer diameter of stent 10 (shown on the x-axis). For much of the working range of diameters for the stent, the diameter increases substantially with little increase in radial force as first cells 94 are opened. Once the first cells 94 finish opening, a significant increase in force is required to open second cells 96 in order to further increase the diameter of the stent.

While FIG. 1 shows one embodiment of the stent, other embodiments of the stent use a first cell with a narrow first strut width and a second cell with a second strut width that is wider than the a first strut width. FIGS. 4-7 show some of these embodiments.

Figure 4:
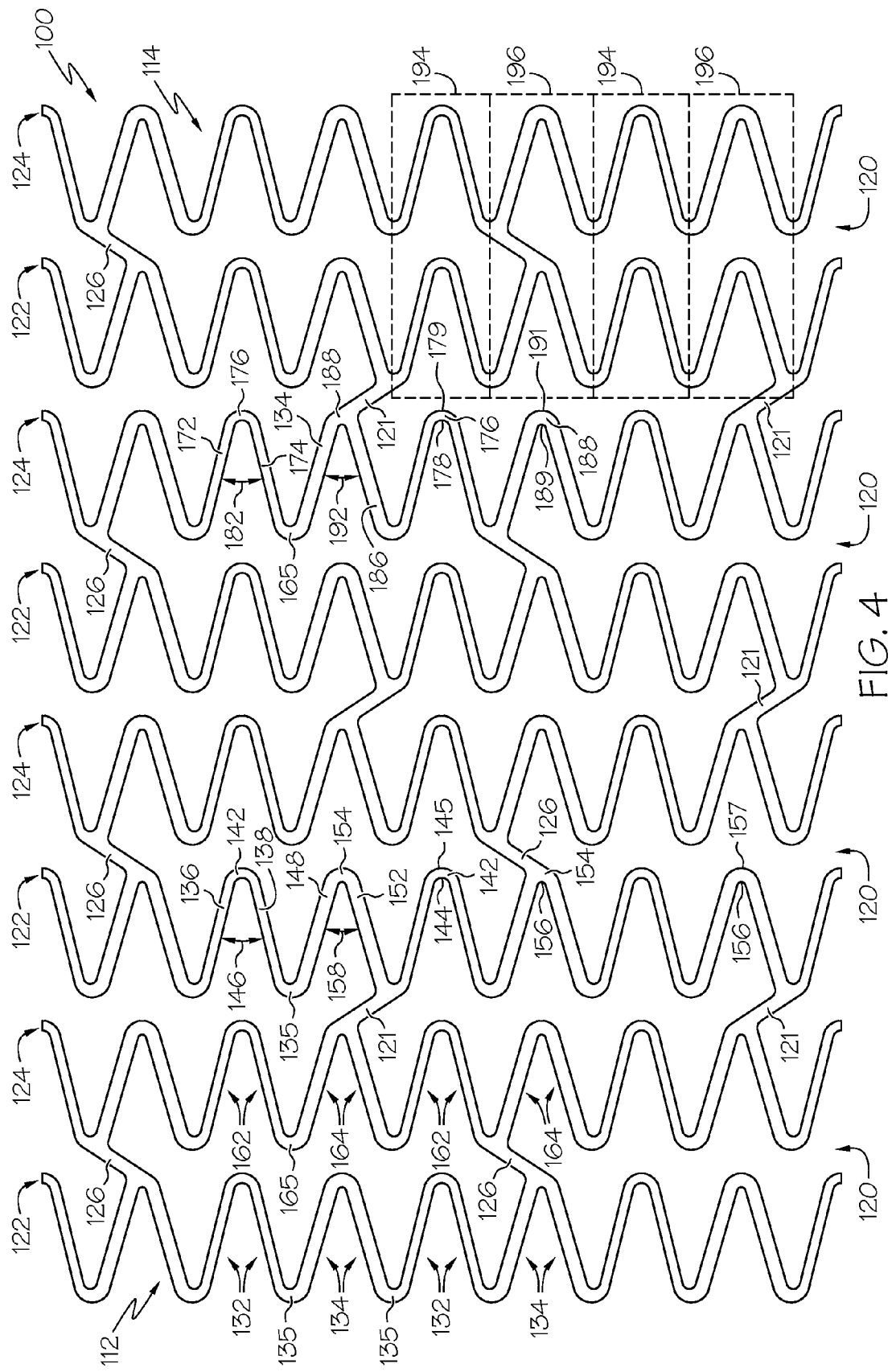
FIG. 4 is a flat view of an embodiment of the stent.

FIG. 4 shows a flat view of an embodiment of a stent of the present invention, stent 10, in an unexpanded state. Stent 100 shown in FIG. 4 is very similar to stent 10 shown in FIG. 1, except that stent 100 has fewer connecting struts 126 and the connecting struts 126 join first serpentine band 122 with second serpentine band 124 differently than connecting struts 26 of stent 10. In FIG. 4, connecting struts 126 join a linking member of a strut pair (such as member 154 of strut pair 134) with a connecting member, such as connecting member 165 that joins a first strut pair 162 with a second strut pair 164. The interconnecting struts 121 also join a first expansion column 120 with a second expansion column 120. However, in FIG. 4, the interconnecting struts 121 join a linking member of a strut pair (such as member 154 of strut pair 164) with a connecting member, such as connecting member 135 that joins a first strut pair 132 with a second strut pair 134. In the embodiment shown in FIG. 4, opening angles 146, 158, 182, 192 all open in the same direction. As shown, this direction is towards proximal end 112; however, in another embodiment, all opening angles 146, 158, 182, 192 can open towards distal end 114.

As with stent 10, thicker-walled second cells 196 alternate with at least one thinly-walled first cell 194 along expansion column 120. In the embodiment shown, first cell 194 has a narrower strut width than second cell 196. In other embodiments, stent 100 can have struts 136, 138, 172, 174 of first cell 194 with thinner wall thicknesses than struts 148, 152, 184, 186 of second 196; struts 136, 138, 172, 174 of first cell 194 can be longer than struts 148, 152, 184, 186 of second cell 196; or combinations thereof. Once a radially expansive force is applied to stent 100 during deployment (such as with a balloon or via self-expansion or both), first cells 194 will begin to open or expand such that the opening angle 146 between first strut 136 and second strut 138 (and, likewise, the opening angle 182 between first strut 172 and second strut 174) increases. Second cells 196 will still not open until an additional radially expansive force is applied, as previously discussed with respect to stent 10.

Figure 5:
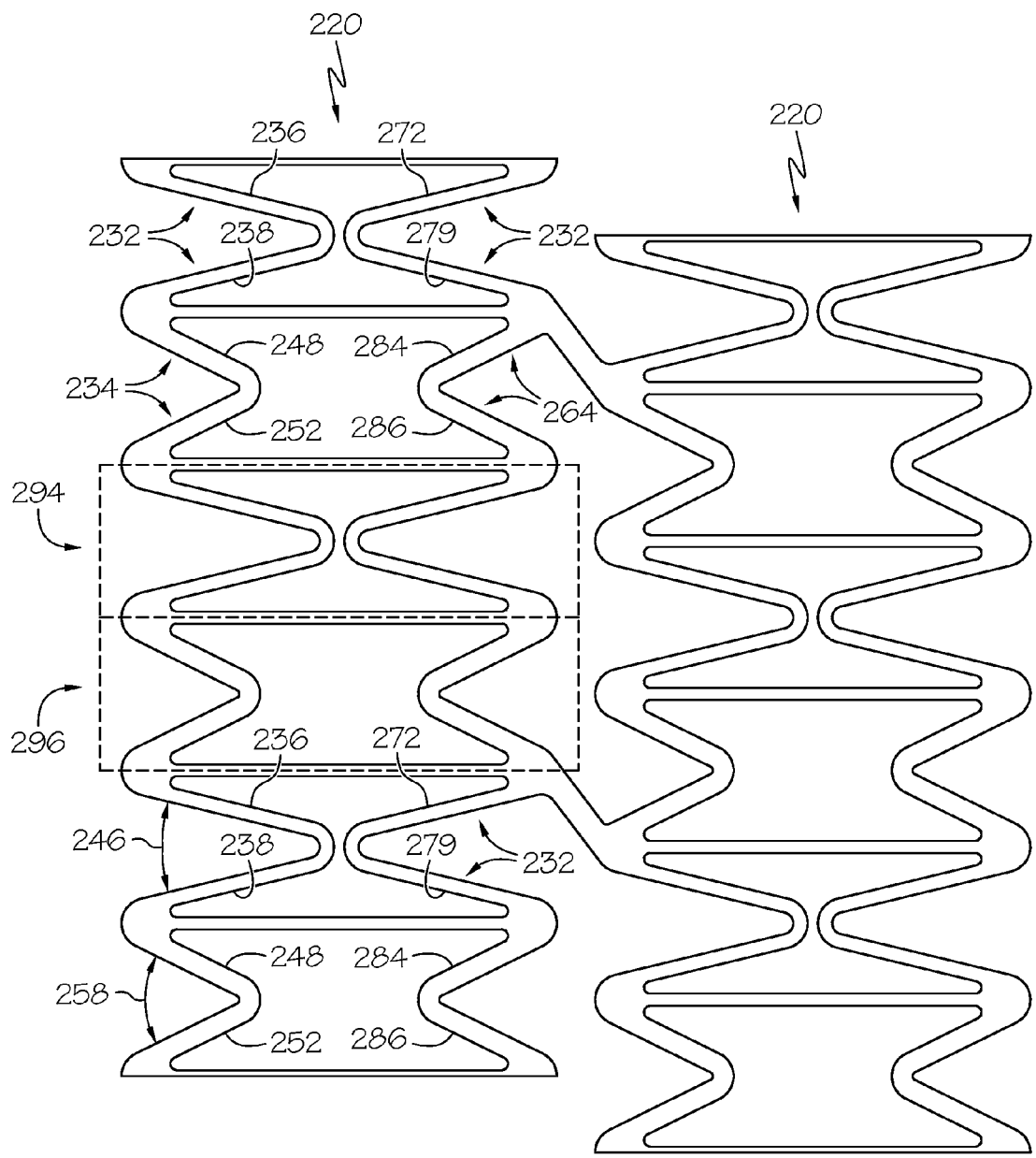
FIG. 5 is a flat view of an embodiment of the stent.

FIG. 5 shows an embodiment of a stent of the present invention. Stent 200 shown in FIG. 4 is very similar to stent 10 shown in FIG. 1, except that the struts 236, 238, 272, 274 of first strut pairs 232, 262 have a first length, while the struts 248, 252, 284, 286 of second strut pairs 234, 264 have a second length that is less than the first length. In some embodiments, the difference in length will cause a difference in the opening angles 246, 258 of first strut pairs 232, 262 and the opening angles 282, 292 of second strut pairs 234, 264. The strut pairs of longer length 232, 262 will open easier than the strut pairs of shorter length 234, 264 because the longer struts form a longer lever needing more force to open the strut pair. In stent 10, these lengths were the same for all strut pairs 232, 234, 262, 264 as were opening angles 246, 258, 282, 292. As with stent 10, thicker-walled second cells 296 alternate with at least one thinly-walled first cell 294 along expansion column 220. Once a radially expansive force is applied to stent 200 during deployment (such as with a balloon or via self-expansion or both), first cells 294 will begin to open or expand such that the opening angle 246 between first strut 236 and second strut 238 (and, likewise, the opening angle 282 between first strut 272 and second strut 274) increases. Second cells 296 will still not open until an additional radially expansive force is applied, as previously discussed with respect to stent 10. Because, in stent 200, the struts 248, 252, 284, 286 of second cell 296 of stent 200 are shorter than struts 36, 38, 72, 74 of second cell 96 of stent 100, second cell 296 will use more force to open than when the struts were the same length as the struts 236, 238, 272, 274 of first cell 94 in stent 10.

Figure 6B:
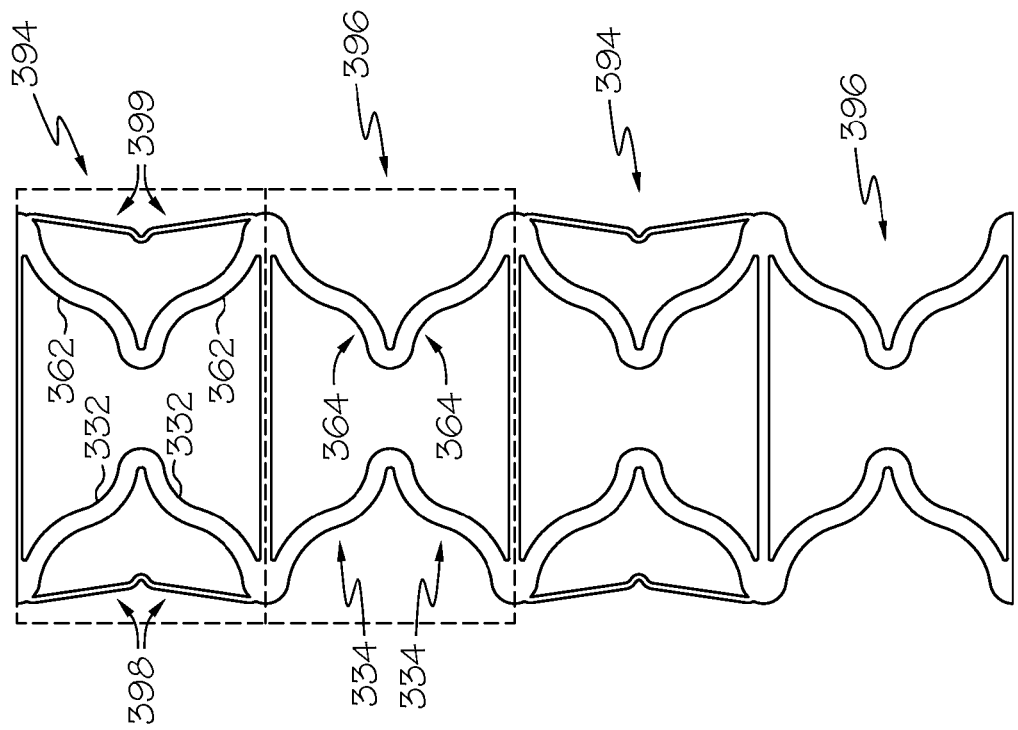
FIGS. 6A-6C show a portion of an expansion column of an embodiment of the stent.
Figure 6A:
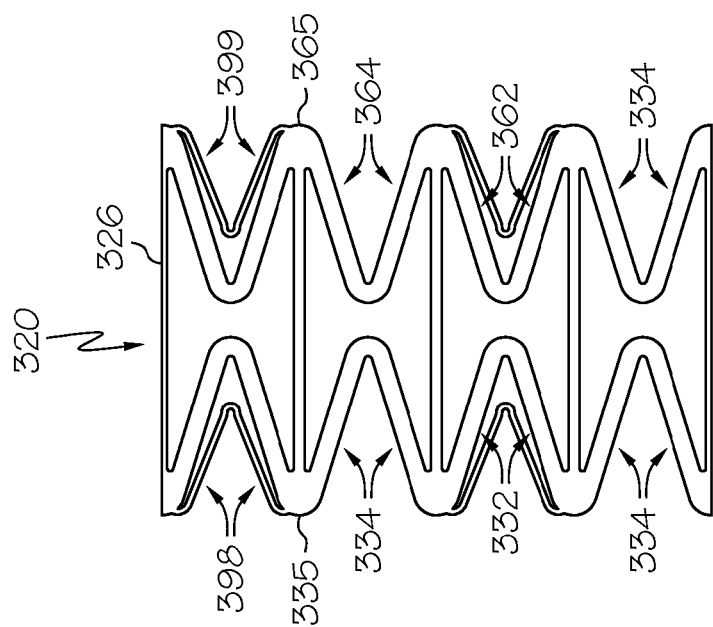
Figure 6C:
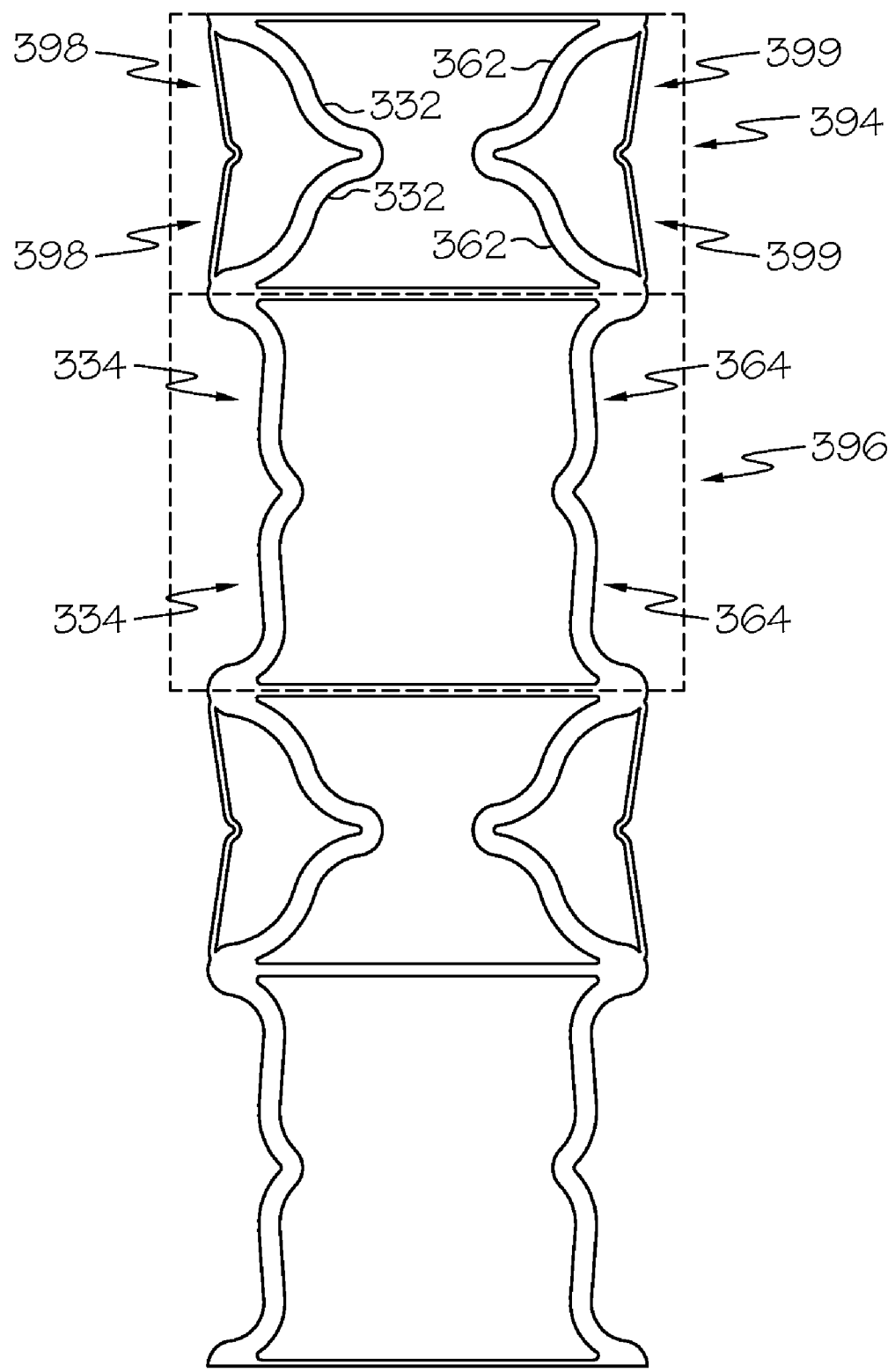
Figure 7:
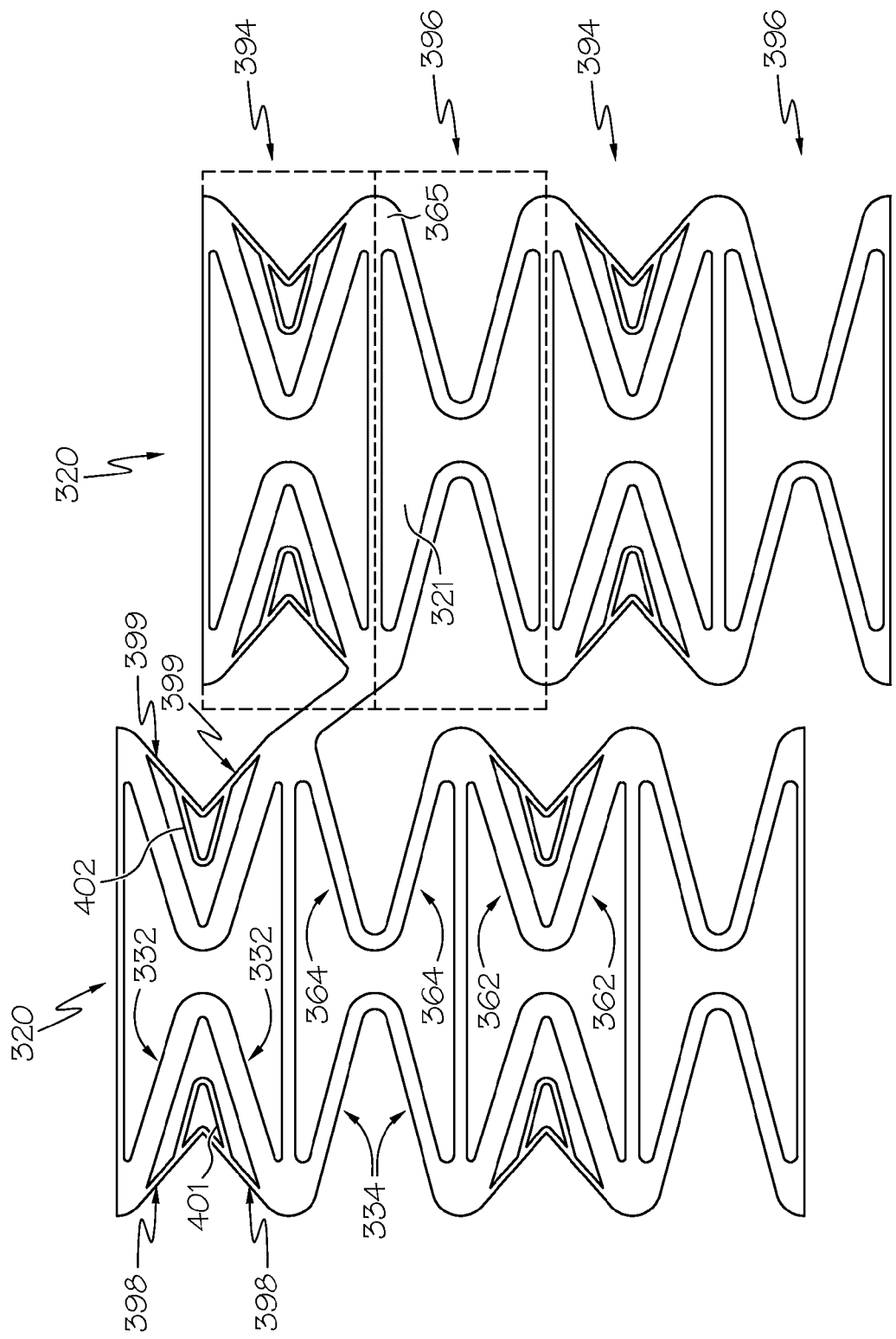
FIG. 7 shows a portion of an embodiment of the stent.

FIG. 6A-6C show a portion of an expansion column 320 of an embodiment of a stent of the present invention. In this embodiment, expansion column 320 of the stent has a third strut pair 398, 399 has been added to each first strut pair 332, 362 of first cell 396. As shown in FIG. 6B, when a radial force is stent 300 expands, third strut pairs 398, 399 form the substantially vertical cell wall for improved radial strength of the stent. Second cells 396 will still not open fully until an additional radially expansive force is applied, as previously discussed with respect to stent 10. If an additional increase in diameter is needed the wall formed by strut pairs 398, 399 can be broken and first cells 394 can open further until first strut pairs 332, 362 form a substantially vertical cell wall for a maximum diameter of the stent. A perforation or notch can be made at certain locations of the strut pairs 398, 399 where when a certain force is reached, the wall formed by strut pairs 398, 399 will break at the notch and release. Other embodiments of this invention, such as the embodiment shown in FIG. 7, have additional wall segments 401, 402 that can break apart to provide for additional expansion of the stent. These additional wall segments are located inside of the strut pairs 398, 399 to allow for additional separation and expansion of the stent, while keeping strut pairs 398, 399 intact.

While the embodiments described above all use narrower and wider strut widths, other embodiments of the invention can be contemplated where the second cells have a greater rigidity, or resistance to opening, than the first cells. For instance, at least one embodiment of the invention has first cells with strut pairs having thinner wall thicknesses and second cells with strut pairs having thicker wall thicknesses such that the wall thicknesses alternate along the circumference of the stent. In at least one embodiment, the stent has alternating cells with larger and smaller strut widths that also alternate with cells having thinner and thicker wall thicknesses. In at least one embodiment, the stent has alternating cells with shorter, wider struts (forming a more rigid cell) with longer, narrower strut lengths (forming a less rigid cell). Furthermore, in at least one embodiment, the stent has cells of alternating material with differences in strength to resist opening.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art can recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent having a proximal end, a distal end, a longitudinal axis extending through the proximal and distal ends, and a circumference, the stent further comprising:
   a plurality of expansion columns, each expansion column extending radially to form the circumference of the stent and comprising a plurality of first cells and a plurality of second cells,
   wherein each second cell alternates with at least one first cell in the expansion column,
   wherein the first cells have at least two facing walls and the second cells have at least two facing walls, wherein the at least two facing walls of the second cells have greater rigidity than the two facing walls of the first cells; and
   a plurality of interconnecting struts axially connecting longitudinally adjacent expansion columns.

2. The stent of claim 1, wherein each of the plurality of first cells comprises at least a first strut pair and each of the plurality of second cells comprises at least a second strut pair, wherein the stent has an as-cut state and at least a first expanded state, wherein, in the first expanded state, the first cell expands such that each strut pair of the first cell expands with a low deployment force to form a substantially vertical member, and wherein thereafter with an application of an additional force, the second cell expands.

3. The stent of claim 1, wherein the first cells have at least two facing walls each having a first width that is less than a second width of at least two facing walls of the second cell.

4. The stent of claim 1, wherein the first cells have at least two facing walls each having a first wall thickness that is less than a second wall thickness of at least two facing walls of the second cell.

5. The stent of claim 4, wherein each of the plurality of first cells comprises at least a first strut pair and each of the plurality of second cells comprises at least a second strut pair, wherein the opening angle of each of the strut pairs of the first cell is greater than the opening angle of each of the strut pairs of the second cell.

6. The stent of claim 4, wherein each of the plurality of first cells comprises at least a first strut pair and each of the plurality of second cells comprises at least a second strut pair, wherein the opening angle of each of the strut pairs of the first cell is equivalent to the opening angle of each of the strut pairs of the second cell.

7. A stent of claim 4, wherein each of the plurality of first cells comprises at least a first strut pair, wherein the stent has an as-cut state and at least a first expanded state, and wherein, in the first expanded state, the first cell expands such that each strut pair of the first cell forms a vertical member.

8. The stent of claim 1, wherein each expansion column has a first serpentine band and a second serpentine band, each serpentine band comprising a plurality of strut pairs having a first strut, a second strut, and an opening angle between the first strut and the second strut, wherein a first strut pair of the first serpentine band and a first strut pair of the second serpentine band form the two facing walls of the first cell, and wherein a second strut pair of the first serpentine band and a second strut pair of the second serpentine band form a second cell.

9. The stent of claim 8, wherein the opening angle of each of the strut pairs of the first cell is greater than the opening angle of each of the strut pairs of the second cell.

10. The stent of claim 8, wherein the opening angle of each of the strut pairs of the first cell is equivalent to the opening angle of each of the strut pairs of the second cell.

11. A stent having a proximal end, a distal end, a longitudinal axis extending through the proximal and distal ends, and a circumference, the stent further comprising:
a plurality of expansion columns, each expansion column extending radially to form the circumference of the stent, each expansion column comprising a first serpentine band and a second serpentine band, each serpentine band comprising a plurality of strut pairs having a first strut, a second strut, and an opening angle between the first strut and the second strut,
wherein a first strut pair of the first serpentine band and a first strut pair of the second serpentine band form a first cell,
wherein a second strut pair of the first serpentine band and a second strut pair of the second serpentine band form a second cell, and
wherein the first strut pair of the first serpentine band is connected to the second strut pair of the first serpentine band,
wherein the first strut pair of the second serpentine band is connected to the second strut pair of the second serpentine band,
wherein the strut pairs of the first cell each have a first strut width and the strut pairs of the second cell each have a second strut width, the first wall thickness being less than the second strut width, and
wherein, in each expansion column, each second cell alternates with at least one first cell along the circumference of the stent; and
a plurality of interconnecting struts axially connecting longitudinally adjacent expansion columns.

12. The stent of claim 11, further comprising:
a plurality of struts that connect the first serpentine band with the second serpentine band within the expansion column.

13. The stent of claim 12, wherein, during the first expanded state, the first cell expands with a low deployment force.

14. The stent of claim 12, wherein the stent has a second expanded state such that the second cell expands under an additional force.

15. A stent having a proximal end, a distal end, a longitudinal axis extending through the proximal and distal ends, and a circumference, the stent further comprising:
a plurality of expansion columns, each expansion column comprising a first serpentine band and a second serpentine band, each serpentine band comprising a plurality of strut pairs having a first strut, a second strut, and an opening angle between the first strut and the second strut,
wherein a first strut pair and a second strut pair of the first serpentine band and a first strut pair and a second strut pair of the second serpentine band form a first cell, the second strut pair circumferentially overlapping the first strut pair,
wherein a third strut pair of the first serpentine band and a third strut pair of the second serpentine band form a second cell,
wherein the opening angle of the first strut pair is less than the opening angle of the second strut pair,
wherein the first strut pair of the first serpentine band and the second strut pair of the first serpentine band are connected to the third strut pair of the first serpentine band at a first connecting node,
wherein, in each expansion column, each second cell alternates with at least one first cell along the circumference of the stent, and
wherein the first strut pair of the second serpentine band and the second strut pair of the second serpentine band are connected to the third strut pair of the second serpentine band at a second connecting node; and
a plurality of interconnecting struts axially connecting longitudinally adjacent expansion columns;
wherein the stent has at least an as-cut state and at least a first expanded state, wherein, in the first expanded state, the first cell expands using a low deployment force until each first strut pair of the first cell forms a vertical member and the second cell is expandable with an additional force.

* * * * *